(12) United States Patent
Bala et al.

(10) Patent No.: US 11,248,251 B2
(45) Date of Patent: Feb. 15, 2022

(54) BIOLOGICAL STERILIZATION INDICATOR

(71) Applicant: American Sterilizer Company, Mentor, OH (US)

(72) Inventors: Harry Bala, South Barrington, IL (US); Richard Koszyk, Chicago, IL (US); Anthony Fiorello, Willowick, OH (US)

(73) Assignee: American Sterilizer Company, Mentor, OH (US)

( * ) Notice: Subject to any disclaimer, the term of this patent is extended or adjusted under 35 U.S.C. 154(b) by 311 days.

(21) Appl. No.: 16/203,180

(22) Filed: Nov. 28, 2018

(65) Prior Publication Data
US 2020/0165658 A1 May 28, 2020

(51) Int. Cl.
*C12Q 1/22* (2006.01)
*A61L 2/28* (2006.01)
*A61L 2/07* (2006.01)
*A61L 2/20* (2006.01)

(52) U.S. Cl.
CPC ................. *C12Q 1/22* (2013.01); *A61L 2/28* (2013.01); *A61L 2/07* (2013.01); *A61L 2/208* (2013.01); *A61L 2202/14* (2013.01)

(58) Field of Classification Search
CPC ..... C12Q 1/22; A61L 2/28; A61L 2/07; A61L 2/208; A61L 2202/14
USPC ..................................................... 435/287.4
See application file for complete search history.

(56) References Cited

U.S. PATENT DOCUMENTS

| | | | |
|---|---|---|---|
| 2,798,856 A * | 7/1957 | Hainsworth | G01N 31/226 436/1 |
| 5,516,648 A | 5/1996 | Malchesky et al. | |
| 7,569,359 B2 | 8/2009 | McDonnell et al. | |
| 8,173,388 B2 | 5/2012 | Pasmore et al. | |
| 2010/0081165 A1* | 4/2010 | Pasmore | C12Q 1/22 435/31 |
| 2013/0230910 A1 | 9/2013 | Christensen et al. | |
| 2015/0004707 A1* | 1/2015 | Nair | A61L 2/28 436/1 |

FOREIGN PATENT DOCUMENTS

| | | |
|---|---|---|
| EP | 0093920 A1 | 11/1983 |
| EP | 2837578 A1 | 2/2015 |
| WO | 9743402 A1 | 11/1997 |

OTHER PUBLICATIONS

International Search Report and Written Opinion issued by ISA/EPO in connection with PCT/US2019/063039 dated Mar. 9, 2020.
International Preliminary Report on Patentability issued by ISA/EPO in connection with PCT/US2019/063039 dated May 25, 2021.

* cited by examiner

*Primary Examiner* — Michael L Hobbs
*Assistant Examiner* — Lenora A Abel
(74) *Attorney, Agent, or Firm* — Levenfeld Pearlstein, LLC

(57) ABSTRACT

A biological sterilization indicator for evaluating the effectiveness of a sterilization process includes a cap containing a culture medium, a container containing a concentration of microorganism, and a breakable barrier attached to the cap to encapsulate the culture medium therein. The breakable barrier is formed from a multilayer structure including an aluminum layer and a sealing layer. The biological indicator is configured such that the breakable barrier may be broken at a selected time by engaging the cap and the container at an activated position to introduce the culture medium into the container.

10 Claims, 4 Drawing Sheets

BIOLOGICAL STERILIZATION INDICATOR

BACKGROUND

The present invention relates to sterilization indicators, and more particularly to biological indicators for verifying the efficacy of a sterilization process.

Medical instruments, surgical instruments, towels (for hospital and operating room use), gowns and the like are sterilized using various different sterilization processes, for example, steam sterilization, sterilization process using gaseous sterilants (e.g., ethylene oxide, vaporized hydrogen peroxide, etc.), and plasma sterilization. The efficacy of sterilization processes may be verified using sterilization indicators. An example of sterilization indicator is a biological indicator including microorganisms (e.g., bacterial spores), a culture medium, and a visible detector to indicate the presence or absence of viable microorganisms.

In use, a biological indicator may be placed in a sterilization chamber with items to be sterilized and subjected to a sterilization cycle. Following the sterilization cycle, the microorganisms is combined with the culture medium and incubated to determine whether any microorganisms survived the sterilization process. The biological indicator may be evaluated visually, for example, by turbidity or a color change, or with a detector, such as spectrophotometer and fluorometer, to measure a selected property, such as pH change, fluorescence, and change in light absorbance.

Biological indicators often employ a system in which a culture medium is separated from microorganisms. For example, the culture medium may be contained in a glass ampoule and disposed in a container housing the microorganisms. Following a sterilization process, the biological indicator may be activated by breaking the ampoule, which releases the culture medium into the container.

U.S. Pat. No. 8,173,388, which is assigned to the Applicant of the present application and incorporated herein by reference, discloses a self-contained sterilization indicator comprising a cap for containing a culture medium and a container housing microorganisms. The cap includes a breakable barrier, which may be broken by engaging the cap with the container at an activated position to introduce the culture medium into the container. Culture medium leakage has been reported in some sterilization processes involving vacuum and high temperatures before the breakable barrier is broken. The present disclosure provides an improved biological indicator configured to reduce a risk of culture medium leakage during sterilization processes.

BRIEF SUMMARY

In one aspect, a biological sterilization indicator for determining the effectiveness of a sterilization process is provided. The biological sterilization indicator may include a container configured to contain a concentration of microorganisms and/or an enzyme, a cap comprising a chamber configured to contain a culture medium and/or a substrate reactive with the enzyme, and a breakable barrier attached to the cap enclosing the culture medium and/or a substrate reactive with enzyme within the chamber. The cultural medium may also be referred to herein as a growth medium. The breakable barrier may be formed from a multilayer structure comprising an aluminum layer and a sealing layer having a thickness of about 0.5 mil to about 3.0 mil.

In an embodiment, the cap may be formed from at least one thermoplastic polymer. For example, the cap may be formed from polypropylene. The sealing layer of the multilayer structure may be formed from a heat sealable material, wherein the sealing layer may be heat sealed to the cap. For example, the sealing layer may comprise polypropylene. The multilayer structure may have a total thickness of about 0.7 mil to about 4.0 mil, in which the aluminum layer has a thickness of about 0.3 mil to about 1.2 mil, and the sealing layer has a thickness of about 0.5 mil to about 3.0 mil. In some embodiments, the aluminum layer and the sealing layer may be laminated with an adhesive layer therebetween.

In an embodiment, the cap may be formed from polypropylene, and the breakable barrier may be formed from a multilayer structure comprising an aluminum layer having a thickness of about 20 μm (0.79 mil) and a sealing layer formed from a homopolymer polypropylene film having a thickness of about 1 mil to about 2 mil.

In some embodiments, the breakable barrier may be formed from a multilayer structure having an outer layer/aluminum layer/tie layer/sealing layer configuration or an outer layer/aluminum layer/tie layer/adhesive layer/sealing layer configuration. In such embodiments, the outer layer may be formed from a nitrocellulose based lacquer coating in weight of about 1.0 g/m$^2$, the aluminum layer may be formed from an aluminum foil having a thickness of about 20 μm (0.79 mil), the tie layer may be formed from a polypropylene based lacquer coating in weight of about 3.5 g/m$^2$, and the sealing layer may be formed from polypropylene, such as a homopolymer polypropylene film having a thickness of about 1 mil or about 2 mil.

The cap may include an outer wall, an upper, closed end, a lower end, an opening adjacent the lower end of the cap, and an inner wall defining the chamber having an opening adjacent the lower end of the cap. The breakable barrier may be heat sealed to the inner wall such that the breakable barrier covers the opening of the chamber.

The container may include at least one puncture member configured to puncture the breakable barrier. The at least one puncture member may be defined by at least one projection arranged within the container.

The cap and the container may be configured to engage with each other in a first position, wherein the breakable barrier is arranged a distance apart from the at least one puncture member. Further, the cap and the container may be configured such that the cap is moveable to a second position, wherein the at least one puncture member comes in contact with the breakable barrier and breaks the breakable barrier to release the culture medium and/or the substrate reactive with the enzyme into the container. The cap and container may be configured to engage each other in a snap-fit relationship or in a screw-thread relationship. At least one of the cap and/or the container may include at least one aperture through which a sterilant enter the container.

Other aspects, objectives and advantages will become more apparent from the following detailed description.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

Figure 1:
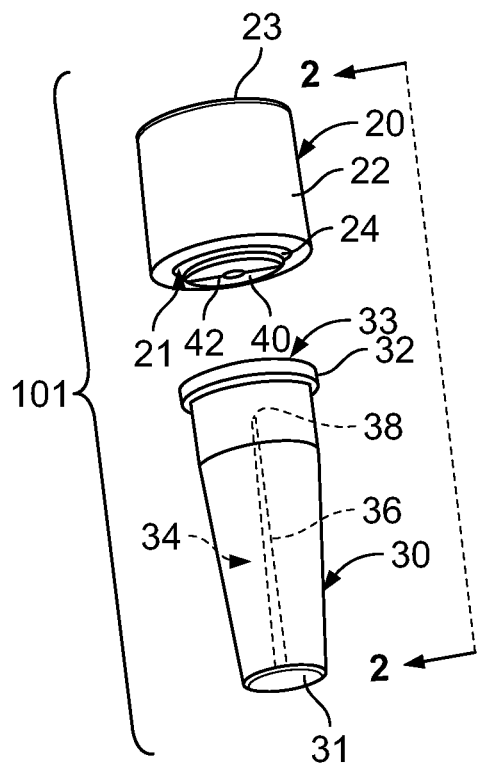
FIG. 1 is a perspective view of a biological sterilization indicator according to an embodiment showing a cap detached from a container.

For simplicity and clarity of illustration, elements shown in the figures may not be drawn to scale. For example, the dimension of some of the elements may be exaggerated relative to each other for clarity.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

It should be further understood that the title of this section of this specification, namely, "Detailed Description Of The Invention", relates to a requirement of the United States Patent Office, and does not imply, nor should be inferred to limit the subject matter disclosed herein.

A biological sterilization indicator system for evaluating a sterilization process according to various embodiments of the present disclosure may generally comprise a cap configured to contain a culture medium and a container configured to contain microorganisms. The cap may include an inner chamber for housing a culture media and a breakable barrier covering the inner chamber and encapsulating the culture medium in the chamber. The breakable barrier may also be referred to herein as a frangible barrier. The media-filled cap may be mountable on the container. The indicator system may be configured such that the breakable barrier may be broken by engaging the cap with the container at an activated position to allow the culture medium to flow into the container containing the microorganisms.

FIGS. 1-4 illustrate a biological sterilization indicator system 10 according to an embodiment. The indicator system 10 may generally comprise a cap 20 that is mountable on a container 30. The container 30 may include a closed, bottom end 31 and an open, upper end 33, and an interior chamber 34 defined therein. The cap 20 may include an outer wall 22, an open, lower end 21, and a closed, upper end 23. The cap also may include an inner wall 24 arranged interior of the outer wall 22 and defining a chamber 26. The chamber 26 may include an opening 25 adjacent to the bottom end of the inner wall 24 and configured to contain a cultural medium 50. The cap 20 may also include a breakable barrier 40 disposed about the opening 25 of the chamber 26 to encapsulate the cultural medium 50 within the chamber 26.

Figure 2:
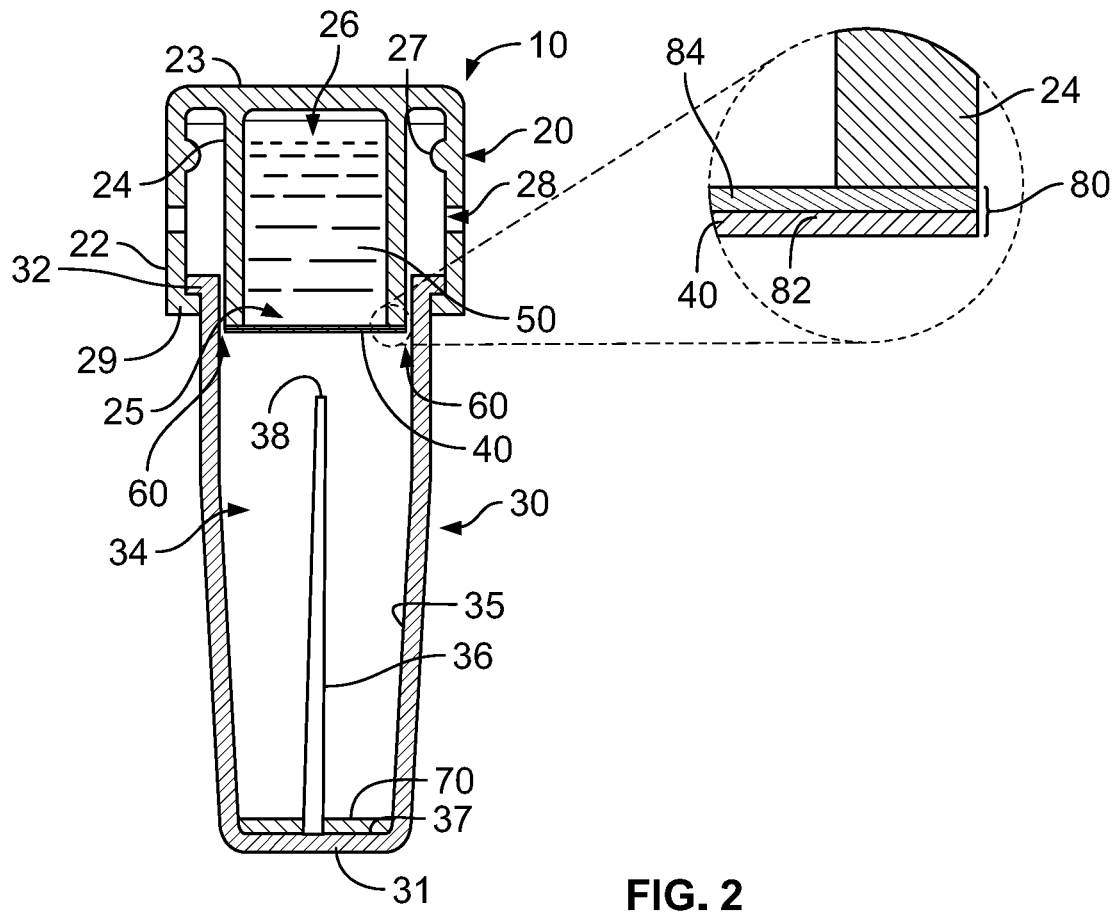
FIG. 2 is a cross-sectional view of the indicator of FIG. 1 taken along line 2-2, in which the cap is mounted on the container in a first, non-activated position.
Figure 3:
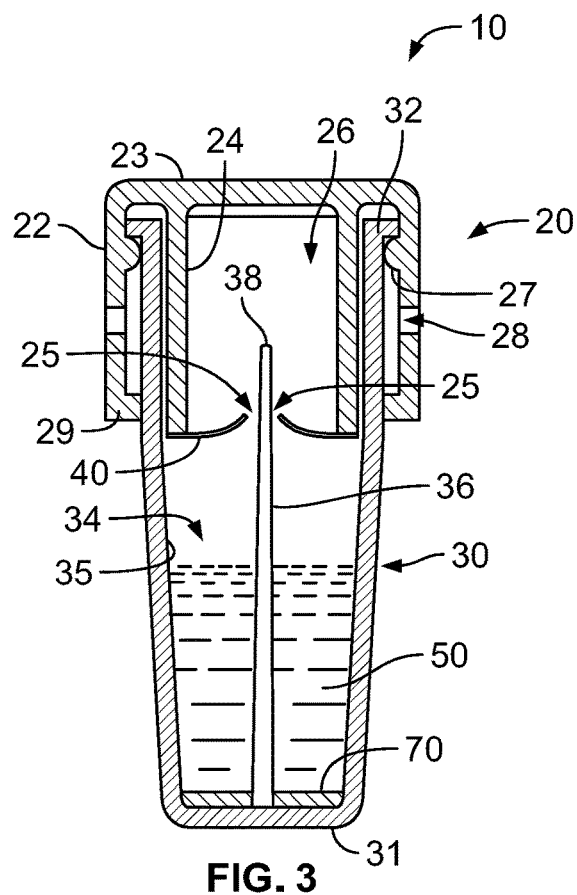
FIG. 3 is a cross-sectional view of the indicator of FIG. 1 taken along line 2-2, in which the cap is mounted on the container in a second, activated position.
Figure 4:
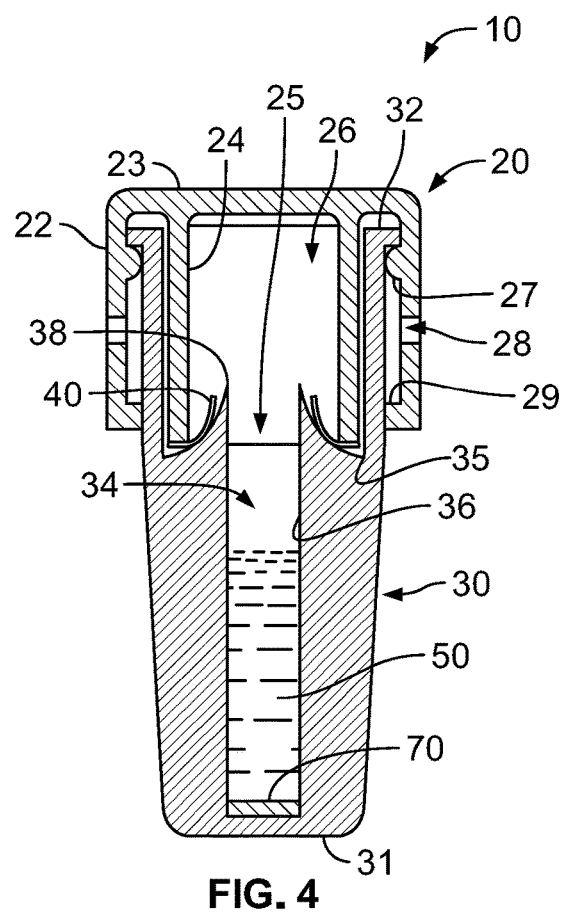
FIG. 4 is a cross-sectional view of the indicator of FIG. 3 rotated by 90°.

In an embodiment, the cap 20 and the container 30 may be configured to engage each other in a snap-fit relationship. As shown in FIGS. 2-4, the container 30 may include an annular projection 32 forming a ridge or lip adjacent or near the upper end 33 of the container. The cap 20 may include an annular projection 29 forming a ridge or lip adjacent the bottom of the cap 20. The cap 20 may be mounted onto the container 30 by sliding the ridge 29 of the cap 20 over the ridge 32 of the container 30. The ridge 32 of the container 30 may be configured to engage the ridge 29 on the cap 20 to prevent the cap 20 and container 30 from decoupling. The cap 20 and container 30 may be configured such that the ridge 32 exerts a sufficient amount of pressure against the cap 20 to prevent the cap 20 from sliding downward without applying an external downward force to the cap 20. In this way, the breakable barrier 40 may be kept spaced apart from edges 38 of puncture members 36 so the breakable barrier 40 does not contact and/or is not broken by the puncture members 36 until such time as desired to activate the indicator system 10.

The puncture members 36 defined by projections arranged in the interior chamber 34 of the container 30 may include edges 38. The edges 38 may be configured to break or puncture the breakable barrier 40 when the cap 20 is pushed down as shown in FIG. 3, such that the puncture members 36 punctures through the breakable barrier 40. The puncture members 36 may be formed integrally with and extending from a side wall 35 and a bottom wall 37 of the container 30. The container 30 may contain a calibrated concentration of microorganisms in the interior chamber 34. The microorganisms may be disposed directly in the interior chamber 34. Alternatively, the microorganisms may be provided on a support member 70 that is disposed in the interior chamber 34.

The cap 20 may have any configuration, shape, and/or size as desired. Further, the configuration, including the shape and/or volume of the chamber 26 may not be limited and may be selected as desired. The breakable barrier 40 may be sealed to the cap 20 to enclose culture medium 50 in the chamber 26 defined in the cap 20. In the illustrated embodiments, the chamber 26 may be filled with culture medium 50, and the breakable barrier 40 may be heat sealed to the bottom surface of the inner wall 24 to enclose the chamber 26 as shown in FIG. 2.

The breakable barrier 40 may be formed from a multilayer structure 80 comprising an aluminum layer 82 and a sealing layer 84. As shown in FIG. 2, the multilayer structure 80 may be attached to the cap 20 with the sealing layer 84 facing the bottom surface of the inner wall 24, such that the sealing layer 84 may be seal to the inner wall 24. The breakable barrier 40 may be seal to the cap 20 using a suitable sealing method, for example, heat sealing, sonic welding, adhesive, etc. The sealing layer 84 may be formed from a suitable polymeric material. Suitable polymeric materials for the sealing layer 84 include, but are not limited to, thermoplastic polymers, such as polypropylene, polyethylene, and blends thereof. The multilayer structure 80 may have a thickness of about 0.7 mil to about 4.0 mil, preferably about 1.5 mil to about 3.5 mil, more preferably about 1.8 mil to about 3.0 mil, wherein the aluminum layer 82 has a thickness of about 0.3 mil to about 1.2 mil, preferably about 0.4 mil to about 1.0 mil, and more preferably about 0.5 mil to about 0.8 mil, and the sealing layer 84 has a thickness of about 0.5 mil to about 3.0 mil, preferably about 0.7 mil to about 2.5 mil, and more preferably about 1.0 mil to about 2.0 mil.

Figure 9:
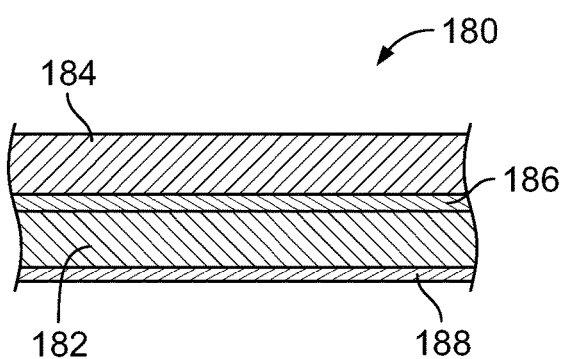
FIG. 9 is a cross-sectional view of a multilayer structure according to an embodiment.

In some embodiments, the breakable barrier 40 may be formed from a multilayer structure comprising more than two layers. For example, the multilayer structure may have an aluminum layer/tie layer/sealing layer configuration, an aluminum layer/adhesive layer/sealing layer configuration, an outer layer/aluminum layer/sealing layer configuration, an outer layer/aluminum layer/tie layer/sealing layer configuration, an aluminum layer/tie layer/adhesive layer/sealing layer configuration, or an outer layer/aluminum layer/tie layer/adhesive layer/sealing layer configuration. The tie layer may be formed from a polymeric material configured to facilitate bonding between the aluminum layer and the sealing layer. FIG. 9 illustrates a multilayer structure 180 comprising a sealing layer 184, tie layer 186, aluminum layer 182, and an outer layer 188. In an embodiment, the multilayer structure 180 may be formed by laminating a lacquer coated aluminum foil with a sealing layer formed from polypropylene. The lacquer coated aluminum foil may comprise an aluminum foil having a thickness of about 20 µm (0.79 mil) coated with a nitrocellulose based lacquer in weight of about 1.0 g/m² on one side and a polypropylene based lacquer in weight of about 3.5 g/m² on the other side, wherein in the sealing layer is laminated to the polypropylene based lacquer side of the lacquer coated aluminum foil. In some embodiments, the lacquer coated aluminum foil and the sealing layer may be laminated with an adhesive layer therebetween.

Figure 5:
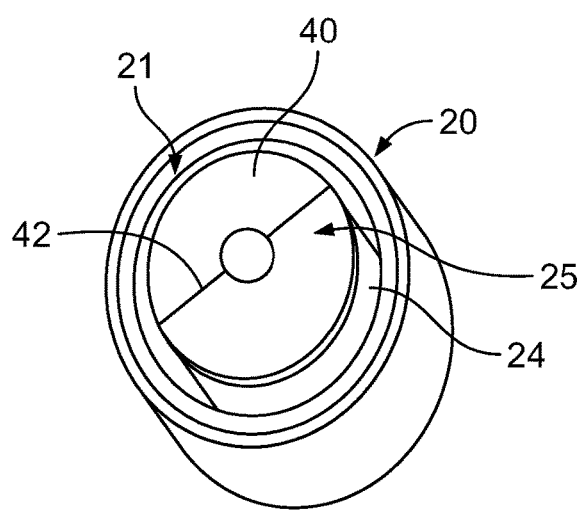
FIG. 5 is a bottom perspective view of the cap from the indicator of FIG. 1.

The breakable barrier 40 may be configured to facilitate puncturing of the breakable barrier 40 by the puncture members 36. For example, the breakable barrier 40 may be provided with an area of weakness. The area of weakness may be defined by, for example, one or more areas in the breakable barrier 40 that are thinner and easier to puncture (i.e., require less force to puncture) relative to the remainder of the breakable barrier 40. The area of weakness may also be provided as a score line, die-cut line, perforated line, or the like in the breakable barrier 40. In the embodiment of FIGS. 1 and 5, the breakable barrier 40 may include a die-cut line 42.

The container 30 may be sized and shaped as desired to suit a particular purpose. As shown in the illustrated embodiments, the container 30 may have a generally conical shape with the side wall tapering toward the bottom of the container. The side wall may be substantially circular in cross section, such that a cross sectional cut nearer the base is of a smaller diameter than a cross sectional cut further away from the base. Further, the geometry of the container's interior may be selected as desired for a particular purpose or intended use. Generally, the interior region is defined by the conical side wall. The interior region may be made smaller by increasing the thickness of the side wall. The geometry of the container may be configured to function as a light path for various detection methods, such as spectroscopic detection methods. Desirably, the light path runs through the container. By providing the container with an interior having a relatively small volume (e.g., tapered geometry in the illustrated embodiments), a smaller volume of culture media is used to concentrate the organisms, metabolites (e.g., enzymes), indicators, and/or substrate molecules. This increases the signal while maintaining an increased path length for the light source.

The cap 20 may be configured to engage the container 30. The engagement or mounting configuration of the cap 20 and the container 30 is not particularly limited. For example, the cap may be mounted to the container in a snap-fit and/or screw-thread relationship. As shown in FIGS. 2-4, the snap-fit configuration may include projections 29, 32 on the cap 20 and the container 30 adapted for engaging one another. The design of such configurations is not limited. Similarly, there is no limitation regarding the design for an indicator system adapted for screw-thread mounting/closure. It will be appreciated that other mounting configurations are also contemplated. For example, an indicator system may be configured with an external latching mechanism or other mechanisms suitable for mounting a cap on a container and activating the indicator system.

As shown, the container 30 may contain at least one puncture member 36 adapted for penetrating or causing the breakable barrier to break when the indicator system 10 is activated. The configuration, size, shape, location, and/or number of puncture members 36 may be selected as desired. For example, the container 30 may include two puncture members 36 that extend from the bottom of the container 30. In other embodiments, the container 30 may include one or more than two puncture members 36 of similar or other configurations.

In use, the indicator system 10 may be assembled by mounting the cap 20 containing the cultural medium 50 on the container 30. The cap 20 may be mounted by snap-fitting the cap 20 onto the container 30. With reference to FIG. 2, the media-filled cap 20 is mounted on the container 30 in a first, non-activated position, wherein the breakable barrier 40 is arranged at a distance apart from the puncture members 36, and thus, is not punctured by the puncture members 36. The indicator system 10 assembled in the first, non-activated position as shown in FIG. 2 may be subjected to a sterilization process. The cap 20 may include apertures 28 through which a sterilant vapor may enter and flow into the indicator system 10. The sterilant may enter the cap 20 through the apertures 28, and flow into the space between the outer wall 22 and the inner wall 24 and into container 30 through a space 60 defined between the cap 20 and the container 30 containing the microorganisms.

After the sterilization process is completed, the indicator system 10 may be activated by pushing down the cap 20 toward the container 30 to a second, activated position. The cap 20 may be moved downward by applying a sufficient downward force or pressure on the cap 20. As the cap 20 moves downward, the breakable barrier 40 may be brought into contact with the edges 38 of the puncture members 36, which punctures or penetrates the breakable barrier 40 as shown in FIGS. 3 and 4. When the breakable barrier 40 is punctured, the opening 25 of the chamber 26 may be exposed, and the culture medium 50 flows into the interior chamber 34 of the container 30 containing the microorganisms. A user may move the cap 20 downward with a twisting motion to affect a greater or maximum opening of the breakable barrier 40 to ensure complete drainage of the culture medium 50 into the container 30.

As shown in FIGS. 3 and 4, the cap 20 may include a second annular projection 27, which may be configured to engage the ridge 32 of the container 30 to hold the cap 20 in the second, closed/activated position. The indicator system 10 may be configured such that the cap 20 and the container 30 are in a sealed relationship in the second, activated position to prevent any new microorganisms from entering the indicator system 10. The indicator system 10 may then be incubated for a predetermined period of time to evaluate the viability of the microorganisms. During incubation, viable microorganisms that survived the sterilization process may metabolize and grow, and release byproducts into the culture medium, which may be detected by a selected property such as pH change, color change, opacity, fluorescence, and the like.

Figure 6:
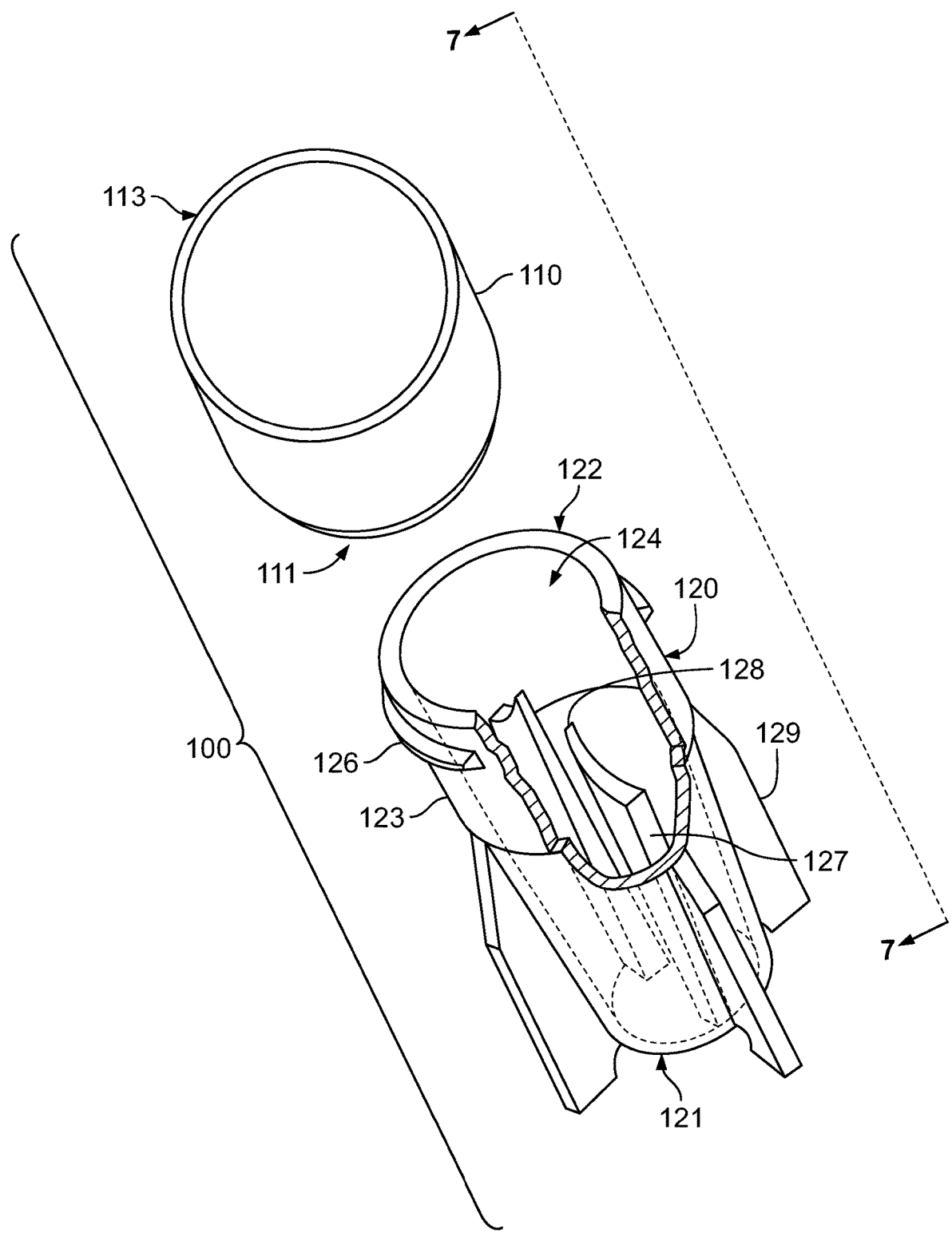
FIG. 6 is a perspective view of a biological sterilization indicator according to another embodiment showing a cap detached from a container.
Figure 7:
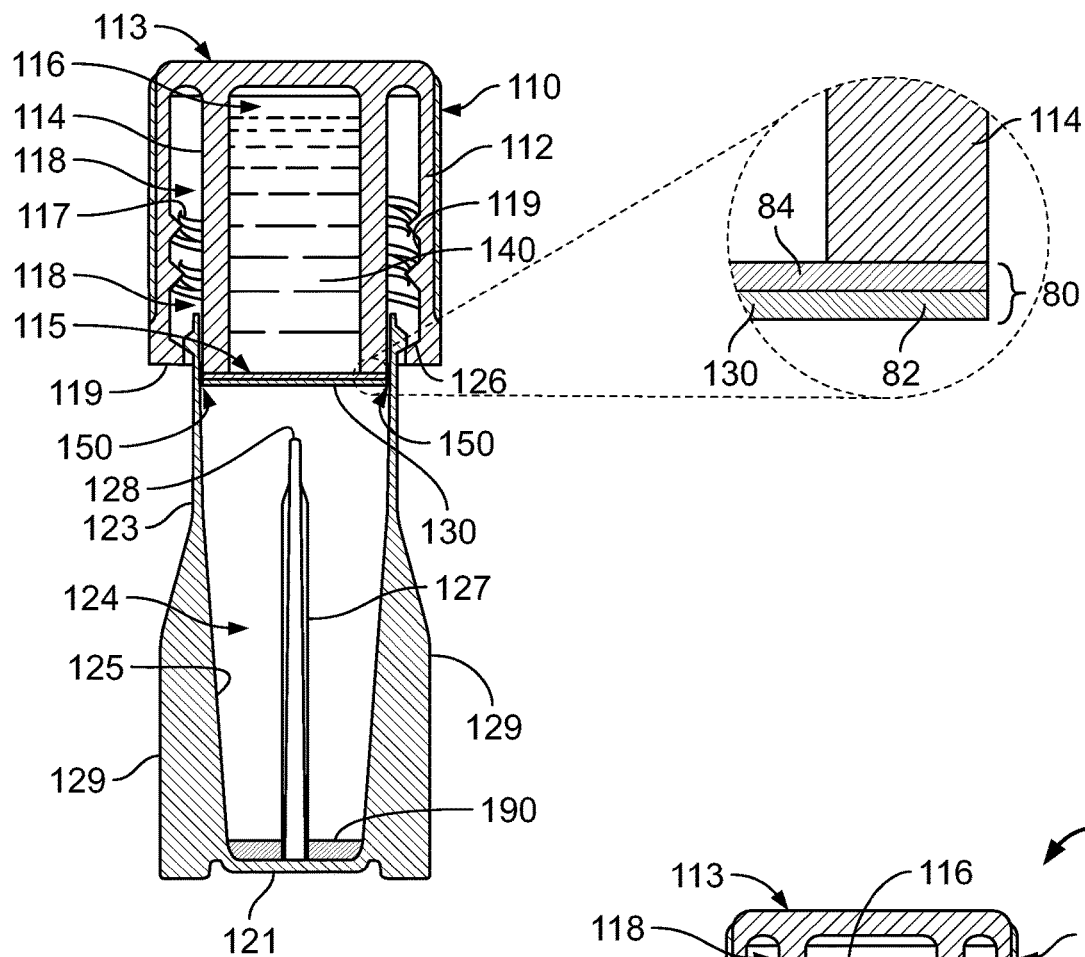
FIG. 7 is a cross-sectional view of the indicator of FIG. 6 taken along the line 7-7, in which the cap is mounted on the container in a first, non-activated position.
Figure 8:
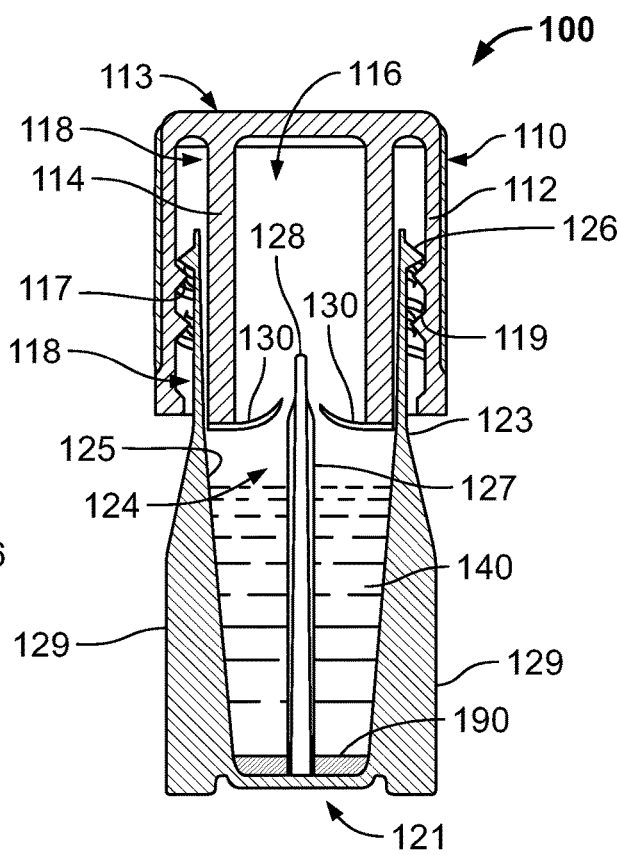
FIG. 8 is a cross-sectional view of the indicator of FIG. 6 taken along line 7-7, in which the cap is mounted on the container in a second, activated position.

FIGS. 6-8 illustrate a biological sterilization indicator system 100 according to another embodiment. The indicator system 100 may be similarly configured to the indicator system 10 of FIGS. 1-5, generally including a cap 110 and a container 120. The cap 110 may include an outer wall 112, a lower, open end 111, a closed, upper end 113, and an inner chamber 116 defined by an inner wall 114 arranged spaced apart from the outer wall 112. The chamber 116 may be configured to contain a culture medium 140. The cap 110 may also include a breakable barrier 130 disposed about an opening 115 to enclose the culture medium 140 within the chamber 116. The breakable barrier 130 may be formed from the multilayer structure 80 comprising the aluminum layer 82 and the sealing layer 84, which may be sealed to the cap 110 as previously described with respect to the embodiment of FIGS. 1-5.

The container 120 may comprise a closed, bottom end 121, an upper, open end 122, a wall 123, and an interior chamber 124 defined therein. The container 120 may also include puncture members 127 having an edge 128 configured to puncture and/or tear the breakable barrier 130. The cap 110 may be configured to engage the container 120 in a screw thread engagement. In such an embodiment, the cap 110 may include an annular projection 117 configured to slide over projections 126 provided on the container 120 to engage the cap 110 with the container 120. The cap 110 may also include a threaded surface on the interior surface of wall 112 defined by the projections 117 and recesses 119. The threaded surface may engage the projections 126 on the container 120 in a screw-thread relationship, and the cap 110 may be moved into a fully closed position by screwing the cap 110 onto the container 120.

The indicator 100 may be used in a manner similar to that described with respect to the previously described indicator 10. Microorganisms may be placed within the interior chamber 124 of the container 120, for example, on a pad 190 and the cap 110 may be mounted on the container 120. The indicator 100 may be subjected to a sterilization process in a first, non-activated position as shown in FIG. 7. The sterilization vapor may enter the cap 110 near the lower end of the cap 110 through a space between the cap 110 and the container 120. For example, in the embodiment depicted in FIGS. 6-10, the projections 126 are discontinuous such that there may be a space or opening between the outer surface of the container 120 and the inner surface of wall 112. The sterilant may pass through this space/opening and flow into space 118 formed between the outer wall 112 and the inner wall 114. The sterilant may pass over and around the projections 117 and over the open end 122 of the container 120 and flow into the container through a passageway 150 defined by a space between the container 120 and the cap 110, and into the interior chamber 124 containing the microorganisms.

After the sterilization process, the indicator system 100 may be activated by moving the cap 110 into a second, activated position as shown in FIGS. 8-9 by screwing the cap 110 onto the container 120. Screwing the cap 110 onto the container 120 may cause the edges 128 of the puncture members 127 to penetrate the breakable barrier 130 to allow the culture medium 140 to drain from the inner chamber 116 of the cap 110 down into the interior chamber 124 of the container 120 containing the microorganisms. As shown in FIGS. 8 and 9, the cap 110 may be moved to a position such that the uppermost thread engages the projections 126 to hold the cap 110 in a sealed relationship with the container 120 to prevent any new microorganisms from entering the indicator system. The indicator system 100 may then be incubated for a predetermined period of time to evaluate the viability of the microorganism.

As shown in the embodiment in FIGS. 6-8, a container 120 may be provided with a support member such as, for example, legs 129. One or more support members may be provided for improved the stability of the indicator. Support members may also provide additional contacting surface for improved heat exchange with a heated surface (e.g., within a sterilization apparatus or with the incubator feature of a detector such as a fluorometer.)

The underside of the container may be provided with a surface geometry suitable for keying the indicator system to a holder for placement in a particular sterilization apparatus, reader, incubator, etc., so that the container can enter a selected holder, reader, incubator, etc. and/or enter the holder, reader, incubator, etc. in a proper orientation. For example, while the legs 129 on the container 120 in FIGS. 6-8 may serve as support members to stabilize and/or support the container, they may also help define a surface geometry along the bottom and sides of the container 120. A holder, reader, incubator, or the like may be provided with a surface having grooves that correspond to the surface geometry/design of the bottom or sides of the container. In other embodiments, the container may not include legs 129. For example, the base of a container, such as the base of bottom end 31 of container 30 in FIGS. 1-4, may be provided with a pattern of grooves, depressions, projections, and the like to provide a particular surface geometry.

The cap 20, 110 and container 30, 120 may be made from a suitable material that can withstand the temperature and/or chemicals employed in a particular sterilization process. Different sterilization techniques may have different material requirements, and the material employed may be selected to suit a particular purpose or intended use. The cap 20, 110 and/or the container 30,120 may be made, for example, from a polymeric material. Suitable polymeric materials include, but are not limited to, polyolefins, polystyrenes, polycarbonates, polymethacrylates, polyimides, polyesters, combinations of two or more thereof, and the like. In an embodiment, at least the inner wall 24, 114 of the cap 20, 110 may be formed from a suitable heat sealable polymeric material for sealing with the breakable barrier 40, 130. Suitable heat sealable polymeric materials include, but are not limited to, polypropylene, polyethylene, and blends thereof. For example, the cap 20, 110 and the container 30,120 may be formed from polypropylene, which is compatible with a variety of sterilants including hydrogen peroxide, steam, ethylene oxide, and peracetic acid.

The cap 20, 110 and the container 30,120 may be manufactured from the same material or they may be manufactured from different materials. For detecting a change in a property of the indicator, the container 30,120 may be configured to have some transparency. For example, for fluorometric and spectroscopic detection methods, the container 30, 120 may be configured to have some transparency to the wavelength(s) of interest. In some embodiments, the cap 20, 110 and/or the container 30,120 may be colored.

The test microorganism may be selected as desired based on the sterilization process being evaluated. Generally, the test microorganism should have a high resistance to the sterilization process being evaluated. Bacterial spores are exemplary microorganisms, because they generally have a high resistance to many different sterilization processes. Other suitable microorganisms include yeasts, fungi, and bacteria in the vegetative state. Exemplary bacterial spores include, for example, *Bacillus pumilus, Bacillus coagulans, Bacillus subtilis, Bacillus circulans, Bacillus atrophaeus, Geobacillus stearothermophilus, Deinococcus radiodurans, Aspergillus niger*, and the like. A single type of test microorganisms or combinations of test microorganisms may be used. The concentration of test microorganisms may be selected as desired for a particular purpose. In one embodiment, the concentration of test microorganisms may be in the range of from about $10^5$ to about $10^{10}$ colony forming units (cfu).

As previously described, the test microorganisms may be inoculated on the bottom or on the walls of the container. Alternatively, the microorganisms may be placed on a support, which is then disposed within the container. Any suitable support material may be used including, for example, a cellulose-based support, a glass fiber based support, or a polymeric support. A non-limiting example of a suitable support includes a spore inoculated element that is wrapped in or encapsulated in a microporous, hydrophilic membrane as disclosed in U.S. Pat. Nos. 5,516,648 and 7,569,359, which are incorporated herein by reference.

The culture medium, also referred to as growth medium, may be selected as desired for a particular purpose or intended use. Examples of suitable culture media include aqueous solutions of soybean-casein digest broth, Dextrose Tryptone, and fluid thyoglycollate. An exemplary culture medium is Tryptic Soy Broth (TSB). In steam or dry heat applications, agar-based media may be used. Agar-based media are generally semi-solid at room temperature, and upon exposure to steam or dry heat, the agar melts. Upon activation of the indicator, the breakable barrier is broken and melted agar flows into the container that contains the test microorganisms and generally remains liquid at the temperatures used for monitoring.

The culture medium may comprise an indicator that undergoes a property change, which is capable of being detected and/or measured, in response to the growth of a particular microorganism. For example, the detector may be provided to react with a particular metabolite (e.g., an enzyme) produced by the growing microorganisms, which results in a color change, a pH change, a pH and a color change, a change in fluorescence (e.g., fluorescing or fluorescence), a change in turbidity, and the like. The metabolite may be selected for relatively quick or early detection of microorganism activity. The indicator may be present in an amount sufficient to provide detectable quantities of the indicator, in the presence of the metabolite, within a period of about two hours (or less) following the completion of the sterilization process. The indicator may be selected based on the test microorganism being used and the metabolite of interest. Suitable metabolites and an appropriate indicator for detecting the metabolite are readily ascertainable by persons skilled in the art. A non-limiting example of a suitable metabolite of interest is an enzyme such as alpha amylase, which is secreted in bacterium such as *Bacillus subtilis*, proteases, and the like. Suitable indicators include, but are not limited to, biologically active molecules, fluorescent dyes, dyes, chromogenic substances, pigments, acids, bases, radiolabelled compounds, molecules that exhibit fluorescence, molecules that cease to fluoresce, and the like. An exemplary indicator is a fluorescent substrate such as, for example, 4-methylumbelliferyl-α-D-glucopyroside (MUD), 4-methylumbelliferyl-β-D-galactopyronoside (MUG), and the like.

The detection method may be selected based on the property of interest and may include, for example, fluorometric, visual, pH, and spectroscopic detection methods. The detection of a measurable change in an indicator property within an established period of time indicates viability of microorganisms and inadequate sterilization. The absence of a measurable change within the established period of time demonstrates that the sterilization process was lethal to the test microorganisms and, thus, adequate.

The culture medium may also contain a substance that reduces the toxicity of the culture medium toward the metabolite. Suitable toxicity reducing substances include, for example, activated charcoal, bovine serum albumin, a soluble starch, and the like.

While the method of using the sterilization indicator has been described with respect to biological indicators, it will be appreciated that the indicator is not so limited and may be used as an enzymatic indicator, a dual biological/enzymatic indicator, and the like. In one embodiment, the sterilization indicator may be used as an enzymatic indicator. In such an application, an active enzyme may be placed in the container, and a substrate that reacts with the enzyme may be placed in the inner chamber of the cap and sealed within the cap's chamber by the breakable barrier. The active enzyme may be impregnated on a carrier strip and disposed within the container. The indicator is then subjected to a sterilization process. The sterilant enters the container and contacts the active enzyme on the carrier strip. After the sterilization procedure, the indicator may be activated as previously described by moving the cap downward such that the breakable barrier is broken (e.g., by being punctured by the puncture member(s) within the container) and the substrate flows into the container where it can contact the enzyme on the carrier strip.

The effectiveness of the sterilization procedure may be evaluated by evaluating the activity of the enzyme. The enzyme and substrate are chosen such that the substrate reacts with the active enzyme to form a detectable product. Generally, the inactivation of the enzyme will be correlated with the death of test microorganisms in the indicator. The enzyme selected for use in a biological indicator should be at least as resistant (and desirably more resistant) to a sterilization procedure as microorganisms that are likely to be present as contaminants. The enzyme should remain sufficiently active to form a detectable enzyme-substrate product after a sterilization cycle that fails to kill contaminating microorganisms, yet be inactivated by a sterilization cycle that kills contaminating microorganisms. If the sterilization procedure works properly, the enzyme is inactivated during the procedure, and there is no detectable product. If the sterilization procedure does not work properly, the enzyme is not inactivated, and the enzyme will react with the substrate to form a detectable product. The enzyme-substrate product may be detectable as a color change, a fluorescent signal, a luminescent signal, or the like.

The enzyme and substrate are not limited and may be selected as desired for a particular purpose or intended use. A person skilled in the art will be able to ascertain and select an appropriate substrate that will react with an active enzyme to produce a product that is detectable by fluorescence, color change, and the like.

An active enzyme may be obtained from various sources such as (i) the purified, isolated enzyme derived from an appropriate microorganism, (ii) a microorganism to which the enzyme is indigenous or added by genetic engineering, or (iii) a microorganism to which the enzyme has been added during sporulation or growth such that the enzyme is incorporated or associated with the microorganism. Suitable enzymes include enzymes derived from spore-forming microorganisms, such as *Bacillus stearothermophilus* and *Bacillus subtilis*. Enzymes from spore-forming microorganisms that are useful in the biological indicators of the invention include, but are not limited to, β-D-glucosidase, α-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, α-D-galactosidase, β-D-galactosidase, tyrosine aminopeptidase, phenylalanine aminopeptidase, β-D-glucuronidase, α-L-arabinofuranosidase, N-acetyl-B-glucosaminodase, β-D-cellobiosidase, alanine aminopeptidase, proline aminopeptidase and a fatty acid esterase, derived from spore forming microorganisms.

Chromogenic and fluorogenic substrates that react with enzymes to form detectable products, and that are suitable for use in the sterilization indicator of the invention, are known in the art. Substrates may be classified in two groups based on the manner in which they create a visually detectable signal. The substrates in the first group react with enzymes to form enzyme-modified products that are themselves chromogenic or fluorescent. The substrates in the second group form enzyme-modified products that must react further with an additional compound to generate a color or fluorescent signal. A number of fluorogenic substrates for enzymes of diverse origin which are known, commercially available, and have been used in enzymological procedures. Among these are a variety of fluorogenic 4-methylumbelliferyl derivatives (hydrolysable to 4-methylumbelliferone); derivatives of 7-amido-4-methyl-coumarin; diacetylfluorescein derivatives; and fluorescamine.

Useful 4-methylumbelliferyl derivatives include, but are not limited to, 4-methylumbelliferyl-2-acetamido-4, 6-β-benzylidene-2-deoxy-β-D-glucopyranoside; 4-methylumbelliferyl acetate; 4-methylumbelliferyl-N-acetyl-β-D-galactosaminide; 4-methylumbelliferyl-N-acetyl-α-D-glucosaminide; 4-methylumbelliferyl-N-acetyl-β-D-glucosaminide; 2'-(4-methylumbelliferyl)-α-D-N-acetyl neuraminic acid; 4-methylumbelliferyl α-L-arabinofuranoside; 4-methylumbelliferyl-β-L-arabinoside; 4-methylumbelliferyl butyrate; 4-methylumbelliferyl β-D-cellobioside; methylumbelliferyl β-D-N, N'-diacetyl chitobioside; 4-methylumbelliferyl elaidate; 4-methylumbelliferyl β-D-fucoside; 4-methylumbelliferyl α-L-fucoside; 4-methylumbelliferyl β-L-fucoside; 4-methylumbelliferyl α-D-galactoside; 4-methylumbelliferyl β-D-galactoside; 4-methylumbelliferyl α-D-glucoside; 4-methylumbelliferyl β-D-glucoside; 4-methylumbelliferyl β-D-glucuronide; 4-methylumbelliferyl p-guanidinobenzoate; 4-methylumbelliferyl heptanoate; 4-methylumbelliferyl α-D-mannopyranoside; 4-methylumbelliferyl β-D-mannopyranoside; 4-methylumbelliferyl oleate; 4-methylumbelliferyl palmitate; 4-methylumbelliferyl phosphate; 4-methylumbelliteryl propionate; 4-methylumbelliferyl stearate; 4-methylumbelliferyl sulfate; 4-methylumbelliferyl β-D-N, N', N''-triacetylchitotriose; 4-methylumbelliferyl 2,3,5-tri-o-benzoyl-α-L-arabinofuranoside; 4-methylumbelliferyl-p-trimethylammonium cinnamate chloride; and 4-methylumbelliferyl β-D-xyloside.

Examples and Test Results

Sample caps configured similar to the cap 110 of FIGS. 6-8 were formed from polypropylene. In Sample Batch 1, a breakable barrier 40 formed from a lacquer coated aluminum foil, which is available from Amcor under the product description Push Through Foil 112-2093, was heat sealed to each of the sample caps filled with 0.5 mL of a culture medium comprising amino acids, minerals, vitamins, fluorogenic agent, and solvent. The lacquer coated aluminum foil included an aluminum foil having a thickness of about 20 μm (0.79 mil) coated with a nitrocellulose based lacquer in weight of about 1.0 g/m$^2$ on one side and a polypropylene based lacquer in weight of about 3.5 g/m$^2$ on the other side. The lacquer coated aluminum foil was heat sealed to each of the sample caps, such that the polypropylene based lacquer side of the foil is sealed to the inner wall 114 of the cap 110.

In Sample Batch 2, the test samples were prepared similar to the test samples of Sample Batch 1, except the lacquer coated aluminum foil of Sample Batch 1 and a 1 mil polypropylene film were used together as the breakable barrier 40. The polypropylene film was a homopolymer polypropylene film having a thickness of about 1 mil, available from COPOL INTERNATIONAL LTD under the product description HP200 Monolayer CPP Film Series. The test samples were prepared by placing the polypropylene film on top of the sample caps and placing the lacquer coated aluminum foil over the polypropylene film followed by heating sealing. The polypropylene film and the lacquer coated aluminum foil were arranged to provide the breakable barrier 40 having a 1 mil polypropylene film/polypropylene based lacquer coating (about 3.5 g/m$^2$ weight)/20 μm aluminum foil/nitrocellulose based lacquer coating (about 1.0 g/m$^2$ weight) construction. The breakable barrier 40 was heat sealed to each of the sample caps filled with the same culture medium used in Sample Batch 1, such that the 1 mil polypropylene sealing layer is sealed to the inner wall 114 of the cap 110.

In Sample Batch 3, the test samples were prepared similar to the test samples of Sample Batch 2, except the lacquer coated aluminum foil of Sample Batch 1 and a 2 mil polypropylene film were used together as the breakable barrier 40. The 2 mil polypropylene film was a homopolymer polypropylene film having a thickness of about 2 mil, available from COPOL INTERNATIONAL LTD under the product description HP200 Monolayer CPP Film Series. The polypropylene film and the lacquer coated aluminum foil were arranged to provide the breakable barrier 40 having a 2 mil polypropylene film/polypropylene based lacquer coating (about 3.5 g/m$^2$ weight)/20 aluminum foil/nitrocellulose based lacquer coating (about 1.0 g/m$^2$ weight) construction. The breakable barrier 40 was heat sealed to each of the sample caps filled with the same culture medium used in Sample Batch 1, such that the 2 mil polypropylene sealing layer is sealed to the inner wall 114 of the cap 110.

Sample Batches 1, 2, and 3 were processed in a sterilizer at 270° F./4 minute steam sterilization cycle. After the sterilization cycle, the test samples were subjected to deep vacuum in a drying step for about 50 minutes and remained in the closed sterilizer chamber for 20 minutes before being inspected for leakage of the culture medium. Test results are summarized in Table 1.

TABLE 1

Biological Indicator Culture Medium Leakage Test Results

| Leakage | Sample Batch 1 sample size (n) = 23 | Sample Batch 2 sample size (n) = 73 | Sample Batch 3 sample size (n) = 25 |
|---|---|---|---|
| Partial Leak (about 0.2 mL leakage) | 26% | 4% | 0% |
| Full Leak | 30% | 0% | 0% |

As summarized in Table 1, the sample caps heat sealed with the breakable barrier comprising an aluminum layer and a polypropylene sealing layer having a thickness of about 1 mil or 2 mil provided improved sealing properties between the cap and the breakable barrier, and significantly reduced the risk of culture medium leakage during a sterilization process.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A biological sterilization indicator for determining the effectiveness of a sterilization process, the sterilization indicator comprising:
   a container configured to contain a concentration of microorganisms and/or an enzyme;
   a cap comprising a chamber configured to contain a culture medium and/or a substrate reactive with the enzyme; and
   a breakable barrier attached to the cap enclosing the culture medium and/or a substrate reactive with enzyme within the chamber, wherein the breakable barrier is formed from a multilayer structure comprising an outer layer/aluminum layer/tie layer/sealing layer configuration or an outer layer/aluminum layer/tie layer/adhesive layer/sealing layer configuration having a thickness of about 0.5 mil to about 3.0 mil, wherein the outer layer is formed from a nitrocellulose based lacquer coating in weight of about 1.0 g/m$^2$, the aluminum layer is an aluminum foil having a thickness of about 0.5 mil to about 0.8 mil, the tie layer is formed from a polypropylene based lacquer coating in weight of about 3.5 g/m$^2$, and the sealing layer is formed from a heat sealable homopolymer polypropylene film having a thickness of about 1.0 mil to about 2.0 mil,
   wherein the aluminum layer and the sealing layer are laminated with an adhesive layer therebetween, and
   wherein the cap is formed from polypropylene, and
   wherein the sealing layer of the breakable barrier is heat sealed to the cap.

2. The biological sterilization indicator of claim 1, wherein the sealing layer thickness is about 1 mil.

3. The biological sterilization indicator of claim 1, wherein the sealing layer thickness is about 2 mil.

4. The biological sterilization indicator of claim 1, wherein the cap includes an outer wall, an upper, closed end, a lower end, an opening adjacent the lower end of the cap, and an inner wall defining the chamber having an opening adjacent the lower end of the cap, wherein the breakable barrier is heat sealed to the inner wall such that the breakable barrier covers the opening of the chamber.

5. The biological sterilization indicator of claim 1, wherein the container comprises at least one puncture member configured to puncture the breakable barrier.

6. The biological sterilization indicator of claim 5, wherein the at least one puncture member is defined by at least one projection arranged within the container.

7. The biological sterilization indicator of claim 1, wherein the cap and the container are configure to engage with each other in a first position wherein the breakable barrier is arranged a distance apart from the at least one puncture member, and wherein the cap and the container are configured such that the cap is moveable to a second position wherein the at least one puncture member comes in contact with the breakable barrier and breaks the breakable barrier to release the culture medium and/or the substrate reactive with the enzyme into the container.

8. The biological sterilization indicator of claim 7, wherein the cap and container are configured to engage each other in a snap-fit relationship.

9. The biological sterilization indicator of claim 7, wherein the cap and container are configured to engage each other in a screw-thread relationship.

10. The biological sterilization indicator of claim 1, wherein at least one of the cap and/or the container comprises at least one aperture through which a sterilant enters the container.

* * * * *